(12) United States Patent
Shimoe

(10) Patent No.: US 6,905,565 B2
(45) Date of Patent: Jun. 14, 2005

(54) DISPOSABLE SANITARY ARTICLE AND PROCESS FOR PROVIDING SUCH ARTICLE WITH ELASTIC MEMBERS ASSOCIATED WITH LEG-OPENINGS

(75) Inventor: Nariaki Shimoe, Kagawa-ken (JP)

(73) Assignee: UNI-Charm Corporation, Ehime-ken (JP)

( * ) Notice: Subject to any disclaimer, the term of this patent is extended or adjusted under 35 U.S.C. 154(b) by 499 days.

(21) Appl. No.: 10/211,269

(22) Filed: Aug. 5, 2002

(65) Prior Publication Data

US 2002/0193775 A1 Dec. 19, 2002

Related U.S. Application Data

(62) Division of application No. 09/805,566, filed on Mar. 14, 2001, now Pat. No. 6,623,468.

(30) Foreign Application Priority Data

Mar. 27, 2000 (JP) .......................................... 2000-87385

(51) Int. Cl.[7] ............................................... A61F 13/15
(52) U.S. Cl. ...................... 156/161; 156/164; 156/229; 156/267; 156/290
(58) Field of Search ................................ 156/161, 163, 156/164, 229, 250, 267, 269, 290, 291

(56) References Cited

U.S. PATENT DOCUMENTS 5,342,341 A    8/1994 Igaue et al.
5,389,173 A  *  2/1995 Merkatoris et al. .......... 156/161
5,413,654 A  *  5/1995 Igaue et al. .................. 156/161
5,525,175 A  *  6/1996 Blenke et al. ............... 156/161
5,745,922 A     5/1998 Rajala et al.

FOREIGN PATENT DOCUMENTS

| EP | 1 072 243 | 1/2001 |
| JP | 4-317650 | 11/1992 |
| JP | 08-215242 A * | 8/1996 |
| WO | WO 90/09159 | 8/1990 |
| WO | WO-9604874 A1 * | 2/1996 |
| WO | WO 97/00654 | 1/1997 |
| WO | WO 00/02511 | 1/2000 |

* cited by examiner

Primary Examiner—Jeff H. Aftergut
(74) Attorney, Agent, or Firm—Lowe Hauptman & Berner, LLP

(57) ABSTRACT

A disposable sanitary article having elastic members extending to be associated with leg-openings secured under tension to the article along transversely opposite side edge portions of the sanitary article. The transversely opposite side edge portions respectively have first elastic zones extending across a crotch region in the longitudinal direction along a desired length, second elastic zones extending from the first elastic zones into a front waist region along a desired length and third elastic zones extending from the first elastic zones into a rear waist region along a desired length. The sections of the elastic members extending along the second elastic zones and the third elastic zones has values of stretch stress represented by a relationship of the second elastic zones<the third elastic zones or the third elastic zones<the second elastic zones.

3 Claims, 4 Drawing Sheets

DISPOSABLE SANITARY ARTICLE AND PROCESS FOR PROVIDING SUCH ARTICLE WITH ELASTIC MEMBERS ASSOCIATED WITH LEG-OPENINGS

This application is a Divisional of application Ser. No. 09/805,566 filed Mar. 14, 2001, now U.S. Pat. No. 6,623,468.

BACKGROUND OF THE INVENTION

This invention relates to a disposable sanitary article such as a disposable diaper, incontinence pants or training pants and a process for attaching elastic members associated with leg-openings to such a sanitary article.

Japanese Patent Application Publication No. 1992-317650A describes a process for attaching elastic members associated with leg-openings to a sanitary article comprising steps of forming a continuous sheet along its transversely opposite side edge portions with longitudinally continuous adhesive zones, forcibly guiding a plurality of the elastic members associated with the leg-openings to extend under tension across the continuous sheet transversely thereof and bonding them to the continuous sheet in a pattern of sine curves. The elastic members associated with the leg-openings attached to the article by the process disclosed in the Publication present a stretch stress identical in front and rear waist regions except a middle zone of a crotch region.

With the sanitary article in the form of the pull-on type diaper particularly for baby, the diaper is apt to leave a space between the baby's skin and the diaper in a front half of the crotch region due to a brisk movement of the baby. In view of this, the stretch stress of the elastic members associated with the leg-openings is preferably preadjusted to be higher in the front half than in the rear half of the crotch region. With the sanitary article in the form of the open-type diaper, in order to avoid an anxiety that the front waist region of the diaper might slip down during use of the diaper, to facilitate the diaper to be put on the baby's body and to provide a good fit of the diaper to the baby's body, the stretch stress of the elastic members associated with the leg-openings is preferably preadjusted to be higher on the front half of the crotch region provided with a target tape strip than on the rear half of the crotch region provided with a pair of tape fasteners. However, the elastic members associated with the leg-openings attached by the process disclosed in the Publication present a substantially identical stretch stress between the front and rear halves of the crotch region. Such feature does not make the elastic members associated with the leg-openings to have the functions required by both the pull-on type diaper and the open type diaper.

SUMMARY OF THE INVENTION

This invention aims to provide a disposable sanitary article in which a stretch stress of elastic members associated with leg-openings in a front half of a crotch region is different from that in a rear half of the crotch region and a process for attaching these elastic members associated with the leg-openings to such sanitary article.

According to one aspect of this invention, there is provided a disposable sanitary article comprising a liquid-pervious topsheet, a liquid-impervious backsheet and a liquid-absorbent panel disposed between the topsheet and the backsheet to define a front waist region, a rear waist region and a crotch region extending between the front and rear waist regions, a pair of leg-openings being defined at transversely opposite side edge portions of the article, and elastic members being secured under tension to leg-openings along the leg-openings.

The article further comprises the transversely opposite side edge portions of the sanitary article respectively which include first elastic zones extending across the crotch region in the longitudinal direction along a predetermined length, second elastic zones extending from the first elastic zones into the front waist region along a predetermined length and third elastic zones extending from the first elastic zones into the rear waist region along a predetermined length wherein the sections of the elastic members associated with the leg-openings extending along the second elastic zones and the third elastic zones has values of stretch stress represented by a relationship of the second elastic zones<the third elastic zones or the third elastic zones<the second elastic zones.

Another aspect of this invention relates to a process for attaching elastic members associated with leg-openings to a disposable sanitary article which comprises a liquid-pervious topsheet, a liquid-impervious backsheet and a liquid-absorbent panel disposed between the topsheet and the backsheet to define a front waist region, a rear waist region and a crotch region extending between the front and rear waist regions, and the pair of leg-openings being define at transversely opposite side edge portions of the article, comprising the steps of:

(a) feeding a continuous web having transversely opposite side edge portions forward and coating the transversely opposite side edge portions with an adhesive agent to form first adhesive zones and second adhesive zones continuously extending in a longitudinal direction of the continuous web; and (b) feeding first and second elastic members associated with the leg-openings continuously extending in the longitudinal direction and securing sections of the elastic members placed upon the first and second adhesive zones to these zones so that the first and second elastic members extend across the first and second adhesive zones to describe a pair of continuous waveforms in a relationship of lateral symmetry, each of which is convex inward transversely beyond each of innermost side edges of the first and second adhesive zones and then convex outward transversely beyond each of outermost side edges of the first and second adhesive zones, each of the waveforms is further convex in a front or rear half of the zone in which each of the waveforms becomes convex inward transversely extending from an imaginary X-axis bisecting a longitudinal dimension of the zone than the rear or front half of the zone, the first elastic members associated with the one leg-opening lying on the first adhesive zone and the second elastic members associated with the other leg-opening are secured to the continuous web along these adhesive zones and the sections of the first and second elastic members which are convex inward and outward transversely beyond the first and second adhesive zones contract to be converged substantially into single bundles so as to move toward the first and second adhesive zones and are secured to the continuous web.

Of the disposable sanitary articles according to this invention, the article in which the elastic members associated with the leg-openings have a stretch stress preadjusted to be higher in the second elastic zone than in the third elastic zone ensures that the elastic members associated with the leg-openings present a tightening effect around the wearer's thighs which is higher in the front half than in the rear half of the crotch region. Such feature enables the elastic members associated with the leg-openings to meet the function required by the pull-on type diaper principally used by the wearer who is brisk in movement.

Of the disposable sanitary articles according to this invention, the article in which the elastic members associated with the leg-openings have a stretch stress preadjusted to be higher in the third elastic zone than in the second elastic zone can avoid a tendency that the contractile force of the elastic members associated with the leg-openings in the second elastic zone might tend to pull the front waist region of the diaper down toward the crotch region. Such feature facilitates the diaper to be put on the wearer's body, prevents the diaper from shifting out of its proper position during use of the diaper and provides a good fit of the diaper to the wearer's body. In view of this, the elastic members associated with the leg-openings arranged in this manner well meets the function required by the open type diaper.

The process according to this invention for attachment of the elastic members associated with the leg-openings to the sanitary article enables the elastic members associated with the leg-openings to be continuously attached to the backsheet so that any one of the second zone and the third zones of the elastic members may have a stretch stress higher than the other.

DETAILED DESCRIPTION OF THE PREFERRED EMBODIMENTS

Details of a disposable sanitary article and a process for providing such article with elastic members associated with leg-openings will be more fully understood from the description given hereunder with reference to the accompanying drawings.

Figure 1:
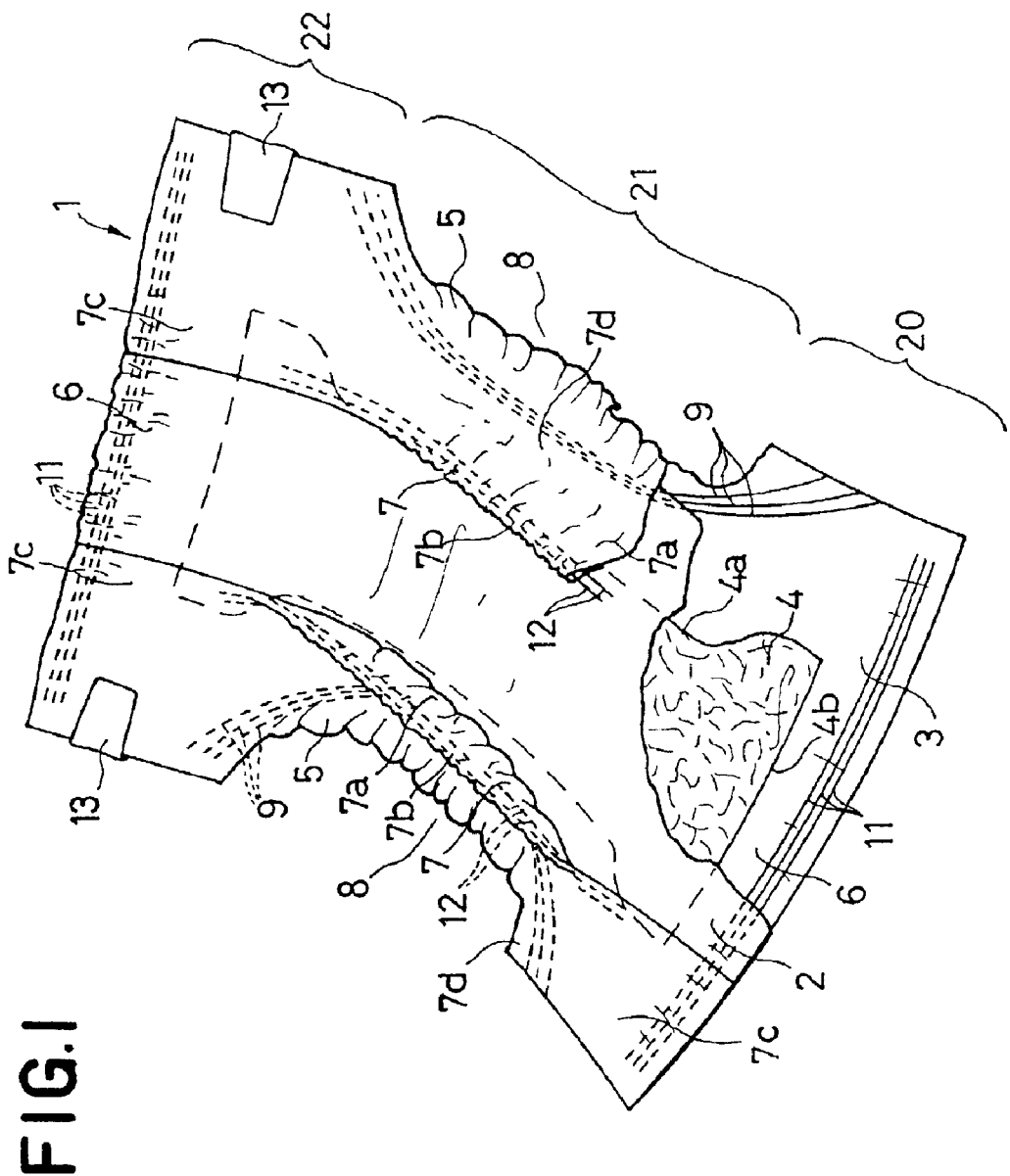
FIG. 1 is a perspective view depicting a partially cutaway disposable diaper as one embodiment of this invention.
Figure 2:
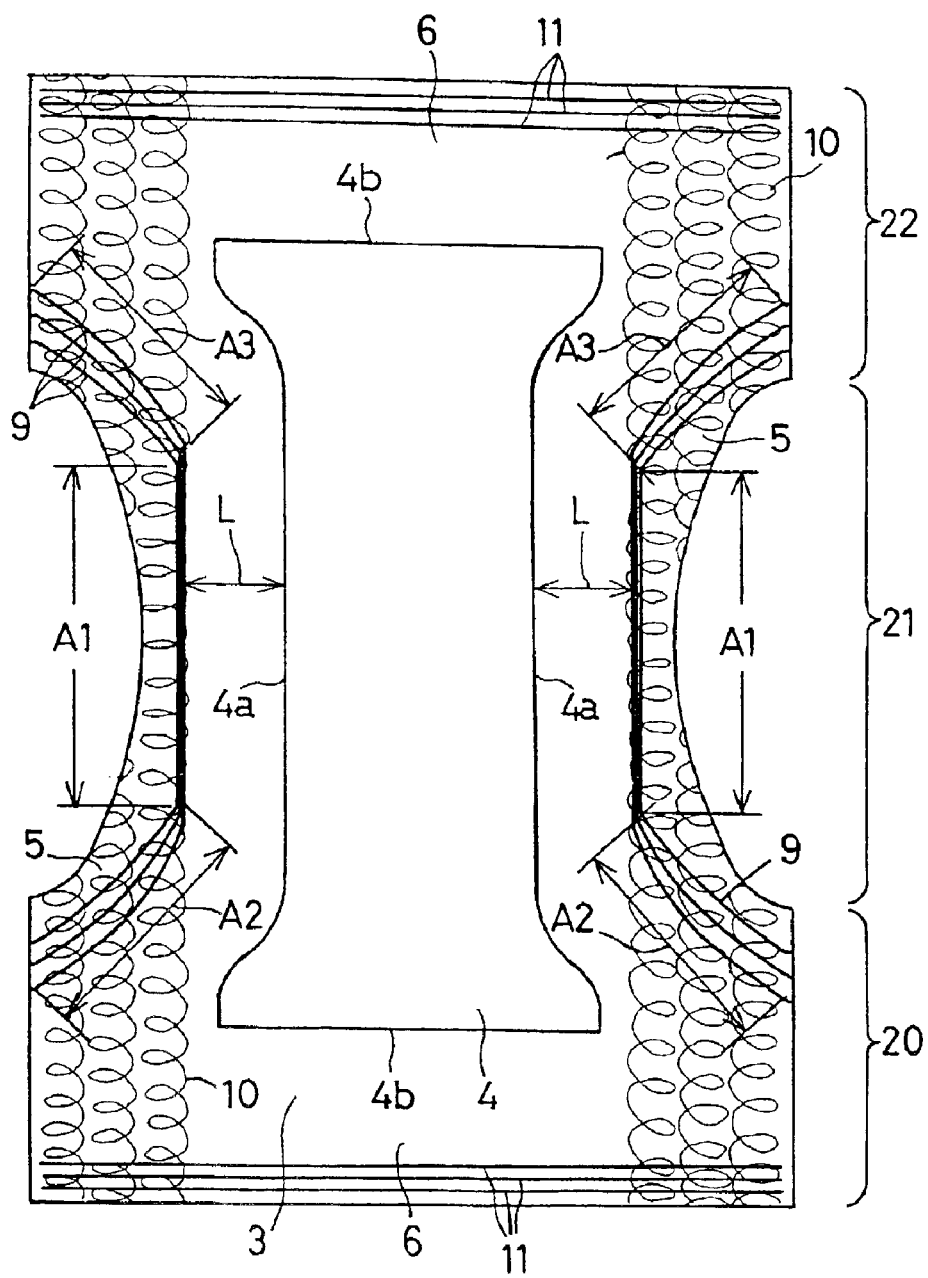
FIG. 2 is a diagram illustrating a relative position of a backsheet, a liquid-absorbent panel and an elastic members.

FIG. 1 is a perspective view depicting a partially cutaway disposable diaper 1 as one embodiment of this invention and FIG. 2 is a diagram illustrating a relative position of a backsheet 3, a liquid-absorbent panel 4 and elastic members 9 in the diaper 1 shown by FIG. 1. As will be best seen in FIG. 2, the backsheet 3 has its inner surface coated with adhesive 10 in a pattern of plural spiral lines longitudinally extending in the vicinity of transversely opposite side edges 5 of the backsheet 3. The diaper 1 comprises a liquid-pervious topsheet 2, the liquid-impervious backsheet 3 and a liquid-absorbent panel 4 disposed between and joined to these two sheets 2, 3. Configurationally, the diaper 1 has a front waist region 20 extending on the side of the wearer's belly, a rear waist region 22 extending on the side of the wearer's hip and a crotch region 21 extending between the front and rear waist regions 20, 22.

The diaper 1 has transversely opposite side edge portions 5 longitudinally extending parallel to each other outside transversely opposite side edges 4a of the panel 4 and longitudinally opposite end portions 6 transversely extending in parallel to each other outside longitudinally opposite ends 4b of the panel 4. The diaper 1 further includes a pair of liquid-resistant side sheets 7 longitudinally extending parallel to each other on the transversely opposite side edge portions 5, namely, being transversely spaced apart from each other.

In the crotch region 21, the respective side edge portions of the diaper 1 are formed with cutouts 8 curving inwardly of the diaper 1 so as to describe circular arcs, respectively. Each of the side edge portions 5 has, along an edge of the cutout 8, a first elastic zone A1 longitudinally extending over a desired length along an intermediate section of the circular arc, a second elastic zone A2 extending from the first elastic zone A1 into the front waist region 20 over a desired length along a section of the circular arc extending aside to the front waist region 20 and a third elastic zone A3 extending from the first elastic zone A1 into the rear waist region 22 over a desired length along a section of the circular arc extending aside to the rear waist region 22. In these elastic zones A1, A2, A3, a plurality of elastic members 9 associated with each of the leg-openings longitudinally extend along the edge of the cutout 8 and are secured under tension to each of the side edge portions 5 with an adhesive agent 10.

Along the longitudinally opposite end portions 6 of the diaper 1, a plurality of elastic members 11 associated with the waist-opening extend transversely of the diaper 1 and are secured under tension thereto. It should be understood that the elastic members 11 associated with the waist-opening may be secured to at least one of the longitudinally opposite end portions 6. It is also possible to use film-like elastic members as the elastic members 11 associated with the waist-opening.

Each of the side sheets 7 has a fixed side edge portion 7a longitudinally extending immediately outside the associated side edge 4a of the panel 4 and joined to the outer surface of the topsheet 2, a free side edge portion 7b longitudinally extending across the crotch region 21 and normally biased to rise on the diaper 1, longitudinally opposite fixed end portions 7c collapsed inward transversely of the diaper 1 and joined to the outer surface of the topsheet 2 in the collapsed state at the longitudinally opposite end portions 6 of the, diaper 1, and an outermost edge portion 7d extending outward from the fixed side edge portion 7a transversely of the diaper 1. A longitudinally extending elastically stretchable member 12 is secured under tension to the free side edge portion 7b of the side sheet 7 so that the stretchable member 12 may be covered with a part of the free side edge portion 7b.

The free side edge portions 7b of the respective side sheets 7 rise on the outer surface of the topsheet 2 as the diaper 1 is longitudinally curved under a contractile force of the elastic members 12. The side sheets 7 rising in this manner function as barrier flaps preventing any amount of excretion discharged on the diaper 1 from leaking sideways. An alternative arrangement is also possible such that the fixed side edge portions 7a are collapsed outward transversely of the diaper 1 and joined to the outer surface of the outermost side edge portions 7d lying on the longitudinally opposite end portions 6 of the diaper 1 in the collapsed state.

Along the transversely opposite side edge portions 5 of the diaper 1, the topsheet 2 is disposed between the backsheet 3 and the respective outermost side edge portions 7d of the side sheets 7 and joined to these sheets 3, 7. The portions of the backsheet 3 and the respective outermost side edge portions 7d of the side sheets 7 extending outward from the topsheet 2 transversely of the diaper 1 are placed upon and are joined to each other. Along the longitudinally opposite end portions 6 of the diaper 1, the topsheet 2 and the backsheet 3 and the side sheets 7 are placed upon and joined one to another. These sheets 2, 3, 7 may be joined one to another using an adhesive agent or a technique of heat-sealing.

In the rear waist region 22, the transversely opposite side edge portions 5 are provided with a pair of tape fasteners 13, respectively, each tape fastener 13 has its proximal end portion attached to the side edge portions 5 so that the tape fastener 13 itself may extend inward transversely of the diaper 1. In the front waist region 20, the backsheet 3 is provided on its outer surface with a rectangular target tape strip (not shown) on which the tape fasteners 13 may be anchored. The respective tape fasteners 13 may be anchored on the target tape strip with a pressure-sensitive adhesive applied on respective inner surfaces of the tape fasteners 13 over their free end portions to form a pair of leg-openings and a waist-opening (both not shown) of the diaper 1.

The panel 4 is semi-rigid and joined to respective inner surfaces of the topsheet 2 and the backsheet 3 preferably with a hot melt adhesive applied in a desired pattern. In order to ensure a stretch stress desired for the elastic members 9 associated with the leg-opening, the panel 4 preferably has a stiffness of 1~300 mN·cm longitudinally as well as transversely of the diaper 1 as measured in accordance with JIS (Japanese Industrial Standards): P-8125 (taber method).

The elastic members 9 associated with the leg-opening along each of the side edge portions 5 extend side by side so that they are converged substantially in a single bundle along the first elastic zone A1 and gradually diverged one from another as they extend into the second elastic zone A2 and the third elastic zone A3. The elastic members 9 associated with the leg-opening have different levels of stretch stress along the second elastic zone A2 and the third elastic zone A3, respectively, in a relationship represented by the second elastic zone A2<the third elastic zone A3. In other words, the stretch stress of the elastic members 9 associated with the leg-opening in the third elastic zone A3 is preadjusted to be higher than that in the second elastic zone A2.

In the diaper 1, the elastic members 9 associated with each of the leg-openings have a stretch stress lower in the second elastic zone A2 than that in the third elastic zone A3 and therefore it is not apprehended that a contractile force of the elastic members 9 associated with each of the leg-openings in the second elastic zone A2 might pull the front waist region 20 of the diaper 1 down toward the crotch region 21. Such a feature advantageously facilitates the diaper 1 to be put on the wearer's body and prevents the diaper 1 from shifting out of its proper position after the diaper 1 has put on the wearer's body. The feature provides a good fit of the of the diaper around the wearer's body.

The stretch stress of the elastic members 9 associated with each of the leg-openings in the first elastic zone A1 is given by a relationship of the first elastic zone A1<the second elastic zone A2. Namely, the stretch stress of the elastic members 9 associated with each of the leg-openings in the first elastic zone A1 is preadjusted to be lower than that in the second elastic zone A2.

In the diaper 1, the contraction of the elastic members 9 associated with each of the leg-openings forms a plurality of gathers in the first elastic zone A1, the second elastic zone A2 and the third elastic zone A3. The number of gathers as well as the depth of each gather in the first elastic zone A1 are less than those in the second elastic zone A2 since the stretch stress of the elastic members 9 associated with each of the leg-openings is lower in the first elastic zone A1 than in the second elastic zone A2. In the wearer's crotch region, therefore, no gap is formed between the wearer's skin and the gathers and leakage of excretion which would otherwise occur along the first elastic zone A1 is reliably avoided.

The length of the first elastic zone A1 is 30~150 mm, preferably 50~100 mm and the stretch stress of the elastic members 9 associated with each of the leg-openings in the first elastic zone is 295~2260 mN/width of 25 mm, preferably 490~1960 mN/width of 25 mm. The stretch stress of the elastic members 9 associated with each of the leg-openings in the second and third elastic zones A2, A3 is 490~2600 mN/width of 25 mm, preferably 780~2450 mN/width of 25 mm. To obtain these values of stretch stress, the side edge portions 5 of the diaper 1 were partially cut out by a width of 25 mm around the elastic members 9 and the sample pieces prepared in this manner were stretched by 88.9%.

In the diaper 1, a dimension L by which the elastic members 9 associated with each of the leg-openings in the first elastic zone A1 are spaced apart from the associated side edge 4a of the panel 4 is preferably in a range of 5~20 mm in the case of the diaper 1 for baby and in a range of 5~60 mm in the case of the diaper 1 for adult. The dimension L less than 5 mm would result in a problem that the stiffness of the panel 4 restricts the contraction of the elastic members 9 associated with the leg-openings. The restricted contraction of these elastic members 9 would result, in turn, in another problem that a tightening effect of the elastic members 9 desired around the wearer's legs may be insufficient to prevent leakage of excretion from occurring in the vicinity of the crotch region 21. In addition, the dimension L less than 5 mm would result in still another problem that the panel 4 may be torsionally deformed or wrinkled as the elastic members 9 contract in the first elastic zone A1.

This invention can be exploited not only in the form of the open type diaper 1 as has been described above but also in the form of the pull-on type diaper. In the case of the pull-on type diaper, though not illustrated, the elastic members associated with each of the leg-openings preferably has a stretch stress in the second elastic zone A2 and the third elastic zone A3 as represented by a relationship of the third elastic zone A3<the second elastic zone A2. Namely, the stretch stress of the elastic members 9 in the second elastic zone A2 is preadjusted to be higher than that in the third elastic zone A3.

Preadjusting the stretch stress of the elastic members 9 associated with each of the leg-openings to be higher in the second elastic zone A2 than in the third elastic zone A3 ensures a desired tightening effect of the elastic member 9 around the wearer's legs particularly in a front section of the crotch region 21. Such feature can be suitably adopted for the pull-on type diaper which is apt to leave a space between the front section of the crotch region 21 and the wearer's skin during use of the diaper.

Figure 3:
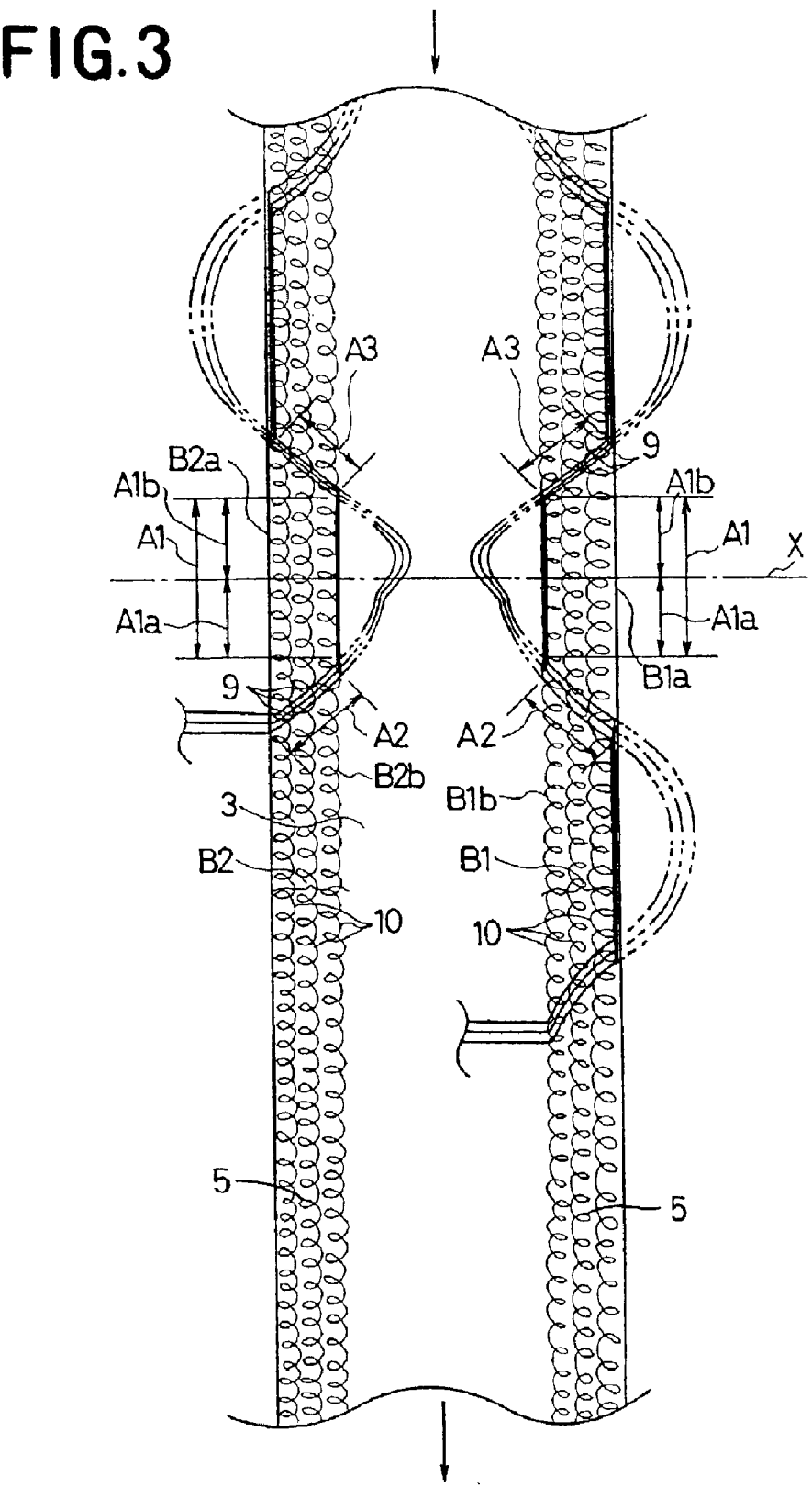
FIG. 3 is a diagram illustrating an example of a process for attachment of the elastic members associated with leg-openings.

FIG. 3 is a diagram illustrating an example of a process for attachment of the elastic members associated with the leg-openings. Referring to FIG. 3, an arrow indicates a direction in which the backsheet 3 travels and chain lines indicate a manner in which first and second elastic members 9 associated with the leg-openings are fed via traverse means 24 (See FIG. 4) while solid lines indicate a state in which the elastic members 9 associated with the leg-openings have been attached to the diaper.

The backsheet 3 is a continuous web having its transversely opposite side edge portions 5 longitudinally extending parallel to each other and continuously fed in its longitudinal direction indicated by the arrow. The inner surface of the opposite side edge portions 5 of the backsheet 3 is applied by adhesive applicator means 23 (See FIG. 4) with a plurality of spiral lines of an adhesive agent 10 longitudinally extending along the transversely opposite side edge portions 5 so as to define first adhesive zone B1 and second adhesive B2 both being continuous in the longitudinal direction.

In the course of being fed in the longitudinal direction, the first and second elastic members 9 associated with the leg-openings are guided by the traverse means to periodically extend across the first and second adhesive zones B1, B2, respectively, and to describe a pair of continuous waveforms longitudinally extend in a relationship of bilateral symmetry. As indicated by the chain lines, the pair of waveforms extend inward beyond respective inner side edges B1$b$, B2$b$ of the first and second adhesive zones B1, B2 transversely of the backsheet 3 and outward beyond respective outer side edges B1$a$, B2$a$ of the first and second adhesive zones B1, B2 transversely of the backsheet 3. Now an X-axis is imagined which bisects a longitudinal dimension of the first zone A1 in which the pair of waveforms are convex inward beyond the respective inner side edges B1$b$, B2$b$ of the first and second adhesive zones B1, B2 transversely of the backsheet 3. The respective waveforms are further convex in a rear half A1$b$ of the first zone A1 longitudinally extending rearward from the imaginary X-axis than in a front half A1$a$ of the first zone A1 longitudinally extending forward from the imaginary X-axis.

The first and second elastic members 9 associated with each of the leg-openings are stretched further inward transversely of the backsheet 3 in the rear half A1$b$ of the first zone A1 than in the front half A1$a$ of the first zone A1 and therefore the third zone A3 has its stretch stress higher than that of the second zone A2.

The first and second elastic members 9 associated with the leg-openings have their second and third zones A2, A3 secured to the first and second adhesive zones B1, B2, respectively, with the values of stretch stress in these elastic zones A2, A3 maintained in a relationship of the second elastic zone A2<the third elastic zone A3.

The contraction of the first and second elastic members 9 associated with the leg-openings causes them to be moved toward the first and second adhesive zones B1, B2 and to be converged substantially into the single bundles until these bundles are substantially straightened along the respective inner side edges B1$b$, B2$b$ of the first and second adhesive zones B1, B2. The respective first zones A1 of the first and second elastic members 9 associated with the leg-openings are secured to the backsheet 3 in the vicinity of the respective inner side edges B1$b$, B2$b$ of the first and second adhesive zones B1, B2.

The contraction of the first and second elastic members 9 associated with the leg-openings causes their respective sections being convex transversely outward beyond the respective outer side edges B1$a$, B2$a$ of the first and second adhesive zones B1, B2 to be moved toward the first and second adhesive zones B1, B2 and to be converged substantially into the respective single bundles until these single bundles are substantially straightened. These straightened sections are then secured to the backsheet 3 in the vicinity of the respective outer side edges B1$a$, B2$a$ of the first and second adhesive zones B1, B2.

The first~third zones A1, A2, A3 of the elastic members 9 associated with the leg-openings illustrated in FIG. 3 correspond to the first~third elastic zones A1, A2, A3 in a manner as will be described. The first zones A1 of the first and second elastic members 9 associated with the leg-openings correspond to the first elastic zones A1 along the transversely opposite side edge portions 5 of the diaper 1 while the second zones A2 of the first and second elastic members 9 associated with the leg-openings correspond to the second elastic zones A2 along the transversely opposite side edge portions 5 of the diaper 1. The third zones A3 of the first and second elastic members 9 associated with the leg-openings correspond to the third elastic zones A3 along the transversely opposite side edge portions 5 of the diaper 1.

The first zones A1 of the elastic members 9 associated with the leg-openings may be stretched at a relatively high ratio to ensure that contraction of said first zones A1 causes said first zones A1 to present the stretch stress lower than those presented by the second and third zones A2, A3 of the elastic members 9 associated with the leg-openings destined to be firmly bonded to the adhesive zones B1, B2. The elastic members 9 associated with the leg-openings are converged and spaced apart from the transversely opposite side edges 4$a$ of the panel 4 as the first zones A1 contract.

After the first and second elastic members 9 associated with the leg-openings have been secured under to the backsheet 3 by following the steps of the process as have been described above, the backsheet 3 may be transversely cut together with these first and second elastic members 9 attached thereto along the lines each extending across the zone in which the first and second elastic members 9 are convex outward beyond the respective outermost side edges B1$a$, B2$a$ of the first and second adhesive zones B1, B2 to obtain a plurality of the backsheet 3 provided with the first and second elastic members 9 firmly bonded thereto.

The process illustrated in FIG. 3 may be appropriately altered in the case of the pull-on type diaper so that the front half of the first zone A1 longitudinally extending forward from the imaginary X-axis is convex further inward transversely of the backsheet 3 than the rear half A1$b$ of the first zone A1 longitudinally extending rearward from the imaginary X-axis is. As a result of this altered arrangement, the first and second elastic members 9 associated with the leg-openings present a stretch stress higher in the respective second zones A2 than in the respective third zones A3 since the elastic members 9 are further stretched in the front half A1$a$ of the first zone A1 than in the rear half A1$b$ of the first zone A1.

The elastic members 9 associated with the leg-openings are attached to the diaper 1 along its transversely opposite side edge portions 5 which may comprise the topsheet 2 and the backsheet 3 or comprise at least one of these sheets 2, 3 and the side sheets 7.

Figure 4:
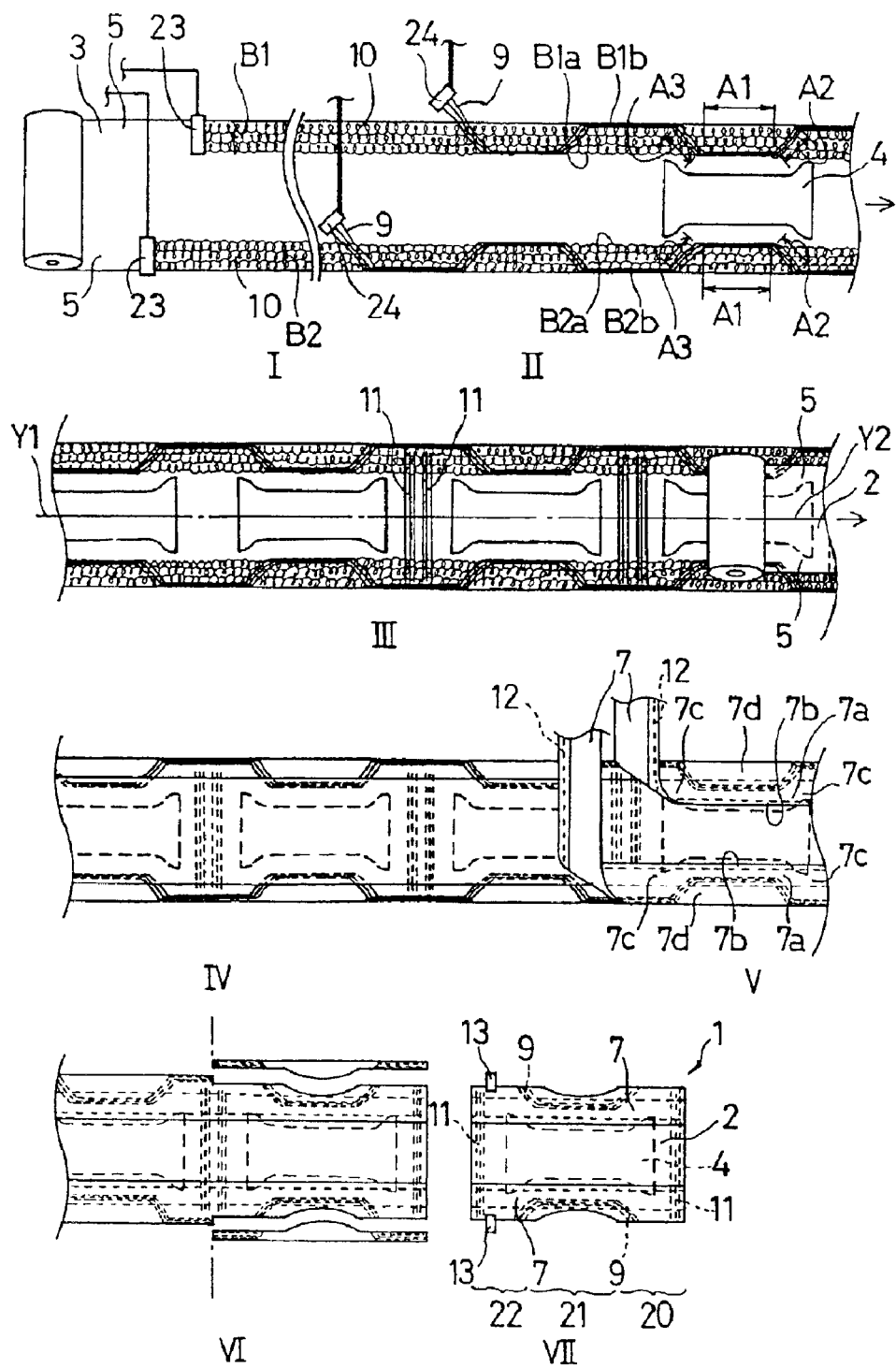
FIG. 4 is a diagram schematically illustrating an example of the process for making the diaper of FIG. 1.

FIG. 4 is a diagram schematically illustrating an example of the process for making the diaper 1 of FIG. 1, including the step of attaching the elastic members 9 associated with the leg-openings to the diaper 1. Respective steps of this process successively proceed in the direction indicated by an arrow. The diaper 1 is made by performing a first step (I)~a seventh step (VII) using, as a stock material, the diaper 1 comprises the topsheet 2, the backsheet 3, the pair of liquid-resistant side sheets 7, the liquid-absorbent panel 4 the elastic members 9 associated with the leg-openings and the elastic members 11 associated with the waist-opening.

Each of the topsheet 2 and the backsheet 3 has the transversely opposite side edge portions 5 longitudinally extending parallel to each other and the backsheet 3 has its transverse dimension larger than that of the topsheet 2. Each of the side sheets 7 is provided along one of its transversely opposite side edge portions defining the free side edge portion 7b with the elastic member 12 which is secured under tension to the side edge portion. The topsheet 2 and the backsheet 3, the side sheets 7 and the elastic members 9 associated with the leg-openings are longitudinally continuous, respectively.

The first step (I) is of feeding the backsheet 3 in its longitudinal direction and coating the inner surface of the backsheet 3 along its transversely opposite side edge portions 5 with adhesive 10. On this first step (I), the backsheet 3 is fed forward from a take-up roll and coated in spiral pattern on the side edge portions 5 with the adhesive agent 10 discharged from nozzles of the adhesive applicator 23. In this manner, the first adhesive zone B1 and the second adhesive zone B2 are formed on the backsheet 3 which are longitudinally continuous, respectively.

The second step (II) is of feeding and bonding the first and second elastic members 9 associated with the leg-openings onto and to the first adhesive zone B1 and second adhesive zone B2, respectively, of the backsheet 3. On this second step (II), a plurality of these first and second elastic members 9 are fed longitudinally of the backsheet 3 via first and second traverse means 24 so that these elastic members 9 extend across the first and second adhesive zones B1, B2 to describe a pair of continuous waveforms in a relationship of lateral symmetry. The elastic members 9 associated with the respective leg-openings are under tension and spaced apart one from another.

The second and third zones A2, A3 of the first and second elastic members 9 associated with the leg-openings lying along the first and second adhesive zones B1, B2 are secured to the backsheet 3 along these adhesive zones B1, B2. Simultaneously, the first zones A1 thereof, which are convex inward beyond the respective innermost side edges B1b, B2b of the first and second adhesive zones B1, B2 transversely of the backsheet 3, contract to be converged substantially into single bundles so as to move toward the first and second adhesive zones B1, B2 and secured to the backsheet 3 along these adhesive zones B1, B2. The sections of the first and second elastic members 9 associated with the leg-openings which are convex outward beyond the respective outermost side edges B1a, B2a of the first and second adhesive zones B1, B2 transversely of the backsheet 3 contract to be converged substantially into single bundles so as to move toward the first and second adhesive zones B1, B2 and secured to the backsheet 3 along these adhesive zones B1, B2. The step diagram of FIG. 3 corresponding to the second step (II) illustrated in FIG. 4 and illustrates the second step (II) of FIG. 4 in details.

The third step (III) is of placing the liquid-absorbent panels 4 on the backsheet 3 along its transversely middle zone and bonding a plurality of transversely extending elastic members 11 associated with the waist-opening to the backsheet 3. On this third step (III), the panels 4 are arranged to be longitudinally spaced apart from one another by a desired dimension so that each of them may be placed between the first and second adhesive zones B1, B2 of the backsheet 3 and joined to the inner surface of the backsheet with an adhesive agent (not shown) applied on the panel 4. The elastic members 11 associated with the waist-opening are placed between respective pairs of the adjacent panels 4 and secured under tension to the inner surface of the backsheet 3 with an adhesive agent (not shown) applied on these elastic members 11.

The fourth step (IV) is of longitudinally feeding and placing the topsheet 2 upon the backsheet 3 and then joining these sheets together on their inner surfaces. On this fourth step (IV), the topsheet 2 is continuously fed from a take-up roll storing the topsheet 2 thereon. The topsheet 2 and the backsheet 3 are placed upon each other with longitudinal center lines Y1, Y2 thereof being maintained in coincidence with each other and joined together with the adhesive agent 10. The panels 4 are joined to the inner surface of the topsheet 2 with an adhesive agent (not shown) applied on these panels 4. To join the sheets 2, 3 together, it is also possible to use a heat-sealing technique instead of using the adhesive agent 10.

The fifth step (V) is of joined the respective side sheets 7 to the marginal portions of the topsheet 2 extending immediately outside the transversely opposite side edges 4a of the panels 4. On this fifth step (V), the respective side sheets 7 put under tension are continuously fed in the longitudinal direction so that the respective fixed side edge portions 7a of the side sheets 7 may be placed immediately outside the transversely opposite side edges 4a of the panels 4. Each of the side sheets 7 has its fixed side edge portion 7a joined to the outer surface of the topsheet 2 with an adhesive agent (not shown) applied on the side sheet 7 and its longitudinally opposite ends 7c collapsed inward transversely and joined to the outer surface of the topsheet 2 in such state with an adhesive agent (not shown). The outermost side edge portion 7d extending outward transversely from the fixed side edge portion 7a is joined to the outer surface of the topsheet 2 and to the inner surface of the backsheet 3 with an adhesive agent (not shown).

The sixth step (VI) is of cutting off respective parts of the backsheet 3, the outermost side edge portions 7d of the side sheets 7 and the first and second elastic members 9 associated with the leg-openings. On this sixth step (VI), the parts of the backsheet 3 and the outermost side edge portions 7d of the side sheets 7 are cut off immediately outside the first and second elastic members 9 associated with the leg-openings describing circular arcs which are convex inward transversely to form the cutouts 8. Then, the parts of the backsheet 3, the outermost side edge portions 7d of the side sheets 7 and the first and second elastic members 9 associated with the leg-openings lying between the respective pairs of the adjacent cutouts 8 are cut off in the vicinity of the outermost side edges B1b, B2b of the first and second adhesive zones B1, B2.

The seventh step (VII) is of transversely cutting the topsheet 2 and the backsheet 3 and the side sheets 7 to obtain individual diapers 1. On this seventh step (VII), the proximal ends of the respective tape fasteners 13 are attached to the outermost side edge portions 7d of the side sheets 7 in the respective rear waist regions 22. Then the topsheet 2 and the backsheet 3 and the side sheets 7 are transversely cut along lines each extending between two groups of the elastic members 11 associated with the respective waist-openings which are adjacent and opposed to each other to obtain the individual diapers 1. Though not shown, the rectangular target tape strips are attached to the outer surface of the backsheet 3 in the respective front waist regions 20 so that the tape fasteners 13 may be anchored on these target tape strips.

While the first step (I) ~ the seventh step (VII) have been described above as these steps are followed to make the open type diaper 1, the same steps may be followed also to make the pull-on type diaper. Obviously, the individual basic diapers 1 can be obtained without the seventh step (VII) of attaching the tape fasteners 13 and the target tape strips. After these basic diapers have been obtained, each of them is folded about its transverse center line bisecting a longitudinal dimension of the diaper 1 with the topsheet 2 inside and the front and rear waist regions 20, 22 thus placed upon each other are joined together in the vicinity of the outermost side edges B1*b*, B2*b* of the first and second adhesive zones B1, B2.

On the second step (II) in FIG. 4, the stretch stress presented by the elastic members 9 associated with the leg-openings is preadjusted to be higher in the third zone A3 than in the second zone A2 for the open type diaper 1 while the stretch stress presented by the elastic members 9 associated with the leg-openings is preadjusted to be higher in the second zone A2 than in the third zone A3 for the pull-on type diaper.

The pattern in which the hot melt adhesive agent 10 is applied in order to attach the elastic members 9 associated with the leg-openings is not limited to the spiral pattern but the other various patterns, e.g., zigzag-, sprayed- and rectilinear-patterns may be used. It is also possible to apply said adhesive 10 along the transversely opposite side edge portions 5 of the backsheet 3 in the form of many dots.

The topsheet 2 may be formed with a liquid-pervious sheet such as a nonwoven fabric or a porous plastic film, preferably by a liquid-pervious hydrophilic sheet. The backsheet 3 may be formed with a hydrophobic nonwoven fabric, a liquid-impervious plastic film of a laminated sheet consisting of a hydrophobic nonwoven fabric and a plastic film, preferably by a breathable but a liquid-impervious sheet. The side sheets 7 may be formed with a breathable but a liquid-impervious nonwoven fabric.

The nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. As the stock material for the backsheet 3 as well as for the side sheets 7, it is also possible to use a composite nonwoven fabric (SMS nonwoven fabric) comprising a melt blown nonwoven fabric having a high water-resistance of which the opposite sheet surfaces are sandwiched between sheet surfaces of a melt blown nonwoven fabric having a high strength and a high flexibility. The component fiber of the nonwoven fabric may be selected from a group including polyolefine, polyester and polyamide fibers and conjugated fiber of polyethylene/polypropylene or polyester.

The panel 4 may be formed with a mixture of fluff pulp and high absorption polymer particles compressed to a desired thickness and then entirely covered with a water-pervious sheet (not shown) such as tissue paper.

This invention is applicable not only to the disposable diaper 1 but also to the incontinence pants or training pants.

What is claimed is:

1. A process for attaching elastic members associated with leg-openings to a disposable sanitary article which comprises a liquid-pervious topsheet, a liquid-impervious backsheet and a liquid-absorbent panel disposed between said topsheet and said backsheet to define a front waist region, a rear waist region and a crotch region extending between said front and rear waist regions, and said pair of leg-openings being defined at transversely opposite side edge portions of said article, comprising the steps of:

(a) feeding a continuous web having transversely opposite side edge portions forward and coating said transversely opposite side edge portions with an adhesive agent to form first adhesive zones and second adhesive zones continuously extending in a longitudinal direction of said continuous web; and (b) feeding first and second elastic members associated with said leg-openings continuously extending in said longitudinal direction and securing sections of said elastic members placed upon said first and second adhesive zones to these zones so that said first and second elastic members extend across said first and second adhesive zones to describe a pair of continuous waveforms in a relationship of lateral symmetry, each of which is convex inward transversely beyond each of innermost side edges of said first and second adhesive zones and then convex outward transversely beyond each of outermost side edges of said first and second adhesive zones, each of said waveforms is further convex in a front or rear half of said zone in which each of the waveforms becomes convex inward transversely extending from an imaginary X-axis bisecting a longitudinal dimension of said zone than said rear or front half of said zone, said first elastic members associated with the one leg-opening lying on said first adhesive zone and said second elastic members associated with the other leg-opening are secured to said continuous web along these adhesive zones and the sections of the first and second elastic members which are convex inward and outward transversely beyond said first and second adhesive zones contract to be converged substantially into single bundles so as to move toward said first and second adhesive zones and are secured to said continuous web.

2. The process according to claim 1, further comprises a step of, after said first and second elastic members have been secured to said continuous web, cutting said continuous web together with said first and second elastic members secured thereto along lines extending across said first and second adhesive zones in which said first and second elastic members become convex outward beyond the outermost side edges of these adhesive zones transversely.

3. The process according to claim 1, wherein said continuous web is a liquid-pervious topsheet or a liquid-impervious backsheet.

* * * * *